United States Patent [19]

Gurske et al.

[11] Patent Number: 4,857,163

[45] Date of Patent: Aug. 15, 1989

[54] HIGH RESOLUTION ELECTROPHORETIC GEL AND METHOD FOR SEPARATING SERUM PROTEINS

[75] Inventors: William A. Gurske, Sunnyvale; Cynthia R. Blessum, Pedley; Min-Lee Cheng, Placentia; Mark S. Andrade, San Diego, all of Calif.

[73] Assignee: Beckman Instruments, Inc., Fullerton, Calif.

[21] Appl. No.: 74,744

[22] Filed: Jul. 17, 1987

[51] Int. Cl.[4] .................. G01N 27/28; G01N 27/26
[52] U.S. Cl. .................. 204/299 R; 204/182.8; 204/180.1
[58] Field of Search ............. 252/315.01, 315.1, 315.3; 204/189, 182.8, 182.9, 182.7, 299 R, 180.1

[56] References Cited

U.S. PATENT DOCUMENTS

| | | | |
|---|---|---|---|
| 4,246,084 | 1/1981 | Gurske | 204/182.8 |
| 4,292,154 | 9/1981 | Ambler | 204/180 |
| 4,319,976 | 3/1982 | Gurske | 204/180 |
| 4,321,121 | 3/1982 | Gurske | 204/180 |
| 4,431,428 | 2/1984 | Schmer | 604/890.1 |

OTHER PUBLICATIONS

Sun, T. et al., *An. Clin. Lab. Sci.*, 8 (3), 219-227 (1978).
Jeppsson, J.-O. et al., *Clin. Chem.*, 25 (4), 629-638 (1979).
Johansson, B. G., *Scand. J. Clin. Lab. Invest.*, 29 (Suppl. 124), 7-19 )1972).
Hock, H. et al., *Anal. Biochem.*, 78, 312-317 (1977).
Howerton, D. A. et al., *Am. J. Clin. Path.*, 85 (2), 213-218 (1986).
Papadopoulos, N. M. et al., *Clin. Chem.*, 28 (4), 707-708 (1982).
Keren, D. F. et al., *Am. J. Clin. Path.*, 85 (3), 348-352 (1986).

*Primary Examiner*—John F. Niebling
*Assistant Examiner*—John S. Starsiak, Jr.
*Attorney, Agent, or Firm*—William H. May; Arnold Grant; Julia E. Abers

[57] ABSTRACT

A novel agarose gel is provided for use in the high resolution electrophoretic (HRE) separation of serum proteins. The agarose gel employs a novel gel buffer which contains either hippurate, glycine, or a mixture thereof, in combination with barbital and Tris. The agarose gel of the present invention yields improved electrophoretic separation of the serum proteins in a sample whether the same gel buffer is also used as the running buffer or whether a standard barbital running buffer is used.

22 Claims, 2 Drawing Sheets

ELECTROPHORETIC SEPARATION USING HIPPURATE GEL BUFFER

ELECTROPHORETIC SEPARATION USING HIPPURATE GEL BUFFER

ELECTROPHORETIC SEPARATION USING GLYCINE GEL BUFFER

ELECTROPHORETIC SEPARATION USING HIPPURATE/GLYCING GEL BUFFER

HIGH RESOLUTION ELECTROPHORETIC GEL AND METHOD FOR SEPARATING SERUM PROTEINS

BACKGROUND OF THE INVENTION

Electrophoresis has become accepted as an important clinical tool for separating serum proteins. Serum proteins are those proteins present in a patient's blood or serum. The amount and type of certain serum proteins present in a patient's sample may be indicative of a disease state or a bodily condition. The clinical significance of all serum proteins is not known.

Electrophoresis involves the motion of dissolved or suspended material under the influence of an applied electric field. Generally speaking, it involves the relative movement between the rigid and mobile parts of an electric double layer.

Most substances acquire a surface electric charge when brought into contact with a polar medium; e.g., an aqueous medium. The possible charging mechanisms include ionization, ion adsorption and ion dissolution. The acquired surface charge influences the distribution of ions in the polar medium; i.e., ions of opposite charge (counter-ions) are attracted toward the surface, and ions of like charge (co-ions) are repelled away from the surface. This, together with the mixing tendency of thermal motion, leads to the formation of an electric double layer made up of: (1) the charged surface; and, (2) a neutralizing excess of counter-ions over co-ions distributed in a diffuse manner in the polar medium.

If an electric field is applied tangentially along the charged surface, a force is exerted on both parts of the electric double layer. The charged surface tends to move in the appropriate direction, bringing along with it any attached material, while the ions in the mobile part of the double layer show a net migration in the opposite direction carrying solvent along with them, thus causing its flow. In electrophoresis, pursuant to the application of an electric field, it is the movement of the charged surface; i.e., dissolved or suspended material, relative to the stationary liquid which is measured. A phenomenon known as electroendosmosis is the complement of electrophoresis, wherein the movement of a liquid relative to a stationary charged surface is measured.

Various substances may be used as support media for electrophoresis. These substances may be divided into two categories for the purpose of separating protein molecules. The first category includes paper, agar or agarose gel, and cellulose acetate, all of which have pores wide enough for the protein molecules to move freely. Electrophoretic methods employing this group of support media generally yield four to seven protein fractions which are included within what is generally regarded as the five "classical" electrophoretic zones; i.e., albumin, $\alpha_1$—, $\alpha_2$—, $\beta$—, and $\gamma$—globulin.

The second category of support media primarily includes polyacrylamide gels. These substances have pore diameters so small that they act as molecular sieves. Consequently, electrophoretic techniques employing these media are able to fractionate proteins according to their molecular volumes as well as their charges, yielding some 20 or more fractions. The high resolving power of these media has proven to be of significant advantage in biomedical research, enabling the isolation and identification of genetic variants in serum proteins. The many bands produced pursuant to polyacrylamide electrophoresis have, however, been found to be inappropriate for routine clinical work. This is because these gel patterns are difficult to read, particularly where they typically contain proteins of unknown clinical significance.

The most popular substances for use in the clinical electrophoresis include agar or agarose gel, cellulose acetate, and paper. These media allow quick separation of serum proteins with reasonably good resolution of the traditional four to seven protein fractions. Agar gel provides the same degree of discrimination among proteins as does filter paper and cellulose acetate, but, unlike these fibrous materials, has the advantages of homogeneity, lack of excessive reticular or network structure, high water retention, translucency, and low adsorptive properties for proteins. Unfortunately, however, electroendosmosis is very strong on agar gel, because of the presence of charged sulfate and carboxyl groups. Consequently, the influence of the agar gel on migration must be controlled by proper placement of samples.

Agar is a mixture of polysaccharides extracted from the cell membrane of certain red seaweeds that are included in the class Rhodophyta of red algae. The main component of agar, is a purified linear galactan hydrocolloid known as agarose. Agarose may be isolated from agar or recovered directly from agar-bearing marine algae. Many undersirable properties of agar are attributed to the high concentration of sulfate ions naturally present in the agar. Agar usually contains from 1 to 5% sulfate, whereas agarose contains less than 0.7%. Practically speaking, agarose is the fraction of heterogenous agar molecules with the lowest charge content and, therefore, the greatest gelling ability.

The isolated agarose, because of its high gel strength at low concentrations, is unique in providing a nearly transparent anticonvection (low electroendosmosis) gel matrix. This unusual property, in addition to the relative inertness and controllable ionic properties of agarose, has led to increased use of agarose gel in clinical applications of electrophoresis.

Nevertheless, agarose gel is yet a relatively new electrophoretic medium. As mentioned, electroendosmosis is minimal, because of the relatively neutral charge characteristics of the agarose. Agarose was first used for gel electrophoresis in 1961, and has rapidly grown in use and applications in recent years. At 1% concentration, the agarose gel network allows rapid and relatively free electrophoretic mobility of proteins with sizes up to more than one million molecular weight, and is therefore very suitable for use in the separation of serum proteins. The agarose medium can be cleared of background stain, and tailing is almost nonexistent. The water content and chemical purity of agarose, being greater than that of cellulose acetate, ensures uniformity of the electrical field and has resulted in sharper separation and definition of the globulin fractions, especially between the $\ominus$— and $\gamma$—globulin.

The scale of operation of agarose gel resembles cellulose acetate rather than paper, and requires only 0.6 $\mu$l of serum. The analysis of an eight-sample gel, including migration time of 40 minutes, drying, staining, and scanning can be completed in about two hours. Agarose gels are ordinarily prepared by heating a suspension of agarose, usually on the order of 1% (w/v), in a buffer solution such as barbital. The agarose gel may also be prepared from a suspension of agarose in deionized water. Such a gel would, however, need to be equilibrated with buffer, similar to the equilibration required for paper or cellulose acetate, prior to running the electrophoretic analysis. Agar or agarose gels which are prepared in a buffer solution do not require equilibration and are sometimes referred to as "prebuffered".

The heating of the agarose suspension is preferably performed on an electric heater equipped with a magnetic stirrer and continues until a clear solution is obtained. The solution is then cooled and spread on a glass plate or plastic sheet. The preparation may be done either manually or automatically. Precast thin agarose gel films which are fixed to a transparent flexible plastic backing and contain eight sample troughs molded into the gel are commercially available from Corning Medical, Palo Alto, California. After sample is applied, the agarose gels are placed in a "running buffer", which may or may not be identical to the buffer solution employed in casting the gel, and an electric potential is applied to run the analysis.

An improved technique of electrophoresis using purified agarose has recently been developed which separates and identifies many more clinically important components than the four to seven conventional fractions, yet does not produce the multiplicity of nonclinically significant bands obtained pursuant to acrylamide protein electrophoresis. Johansson, B. G., Agarose Gel Electrophoresis, *Scand. J. Clin. Lab. Invest.*, 29, (Suppl. 124), 7–19 (1972). The improved technique employs separation of serum proteins in agarose gel on water-cooled glass plates, applying a relatively high voltage, and has resulted in the simultaneous separation of approximately 15 protein samples in less than one hour. In addition, calcium ions are added to the standard barbital running buffer, at pH 8.6, to obtain better resolution of the components in the $\beta$—globulin region and to enhance the staining of globulins.

The use of a high voltage of about 260 V, or 20 v/cm, is considerably more than twice that used in conventional agarose electrophoresis. This high voltage resulted in two or more components of concentrations greater than 50 mg/dl for each of the "classical" electrophoretic zones. Id. The increased amount of heat generated by the high voltage, which otherwise would denature the proteins and damage the agarose gel, is removed from the system by: e.g., circulating cool water at 10° C. It is reported that the use of barbital as the running buffer is superior to tris-glycine buffers and borate buffers, at least in the separation of plasma proteins. Id.

This technique of combining the use of agarose medium, a cooling system, and a modified buffer containing calcium ions, has become known as high-resolution electrophoresis (HRE). HRE has been applied to normal and pathological plasma, with the identification of as many as 14 components that comprise more than 95% of the serum protein mass and have a decisive influence on the appearance of the electrophoretic pattern. Laurell, C. -B., composition and variation of the Gel Electrophoretic Fractions of Plasma, Cerebrospinal Fluid and Urine, *Scand. J. Clin. Lab. Invest.*, 29, (Suppl. 124), 71–82, 1972. At least 11 protein fractions, excluding prealbumin and fibrinogen, are ordinarily identifiable in normal human serum using HRE procedures. Sun, T., The Present Status of Electrophoresis, *Laboratory Management* 17 (6), 43–49 (1979). These 11 fractions correlate with the five "classical" electrophoretic zones as follows:

| Five Zone | HRE |
| --- | --- |
| albumin | albumin |
| $\alpha_1$-globulin | $\alpha_1$-lipoprotein |
|  | $\alpha_1$-antitrypsin |
| $\alpha_2$-globulin | trypsin inhibitor anti-chymotrypsin |
|  | $\alpha_2$-macroglobulin |
|  | hapto globulin |
| $\beta$-globulin | hemopexin |
|  | transferrin |
|  | $\beta$-lipoprotein |
|  | $C_3$ complement |
| $\gamma$-globulin | $\gamma$-globulin |

The HRE pattern is decidedly complex because of the large number of bands of variable staining intensity and zone width, the genetic variants, and the abnormal bands in some pathological states. The subjective interpretation of these patterns still requires considerable experience. Serum is preferred to plasma because the fibrinogen band in plasma is likely to obscure or cause confusion with any electrophoretic immunoglobulin abnormality lying the $\beta$—globulin region. The main value of the pattern is in the visual recognition of changes in staining intensity of the individual fractions from normal, either an increase or decrease, by comparison with a selected normal. These proteins can then be quantified by immunochemical procedures.

Although HRE procedures have provided a significant advance in the routine clinical analysis of serum proteins, it would be advantageous to provide a gel and/or method capable of further clarifying the bands which appear on the HRE gel, thus improving resolution and making the reading of the gels easier. One suggestion in this area is the proposed use of a high concentration agarose gel. Hoch, H. and Lewallen, C. G., High Concentration Agarose Gel: A New Medium for High Resolution Electrophoresis, *Anal. Biochem.*, 7, 312–317 (1977). Gels in the range of 3.5 to 15% agarose (g/l), made up in sodium phosphate buffer, were reported to have superior resolving power to the more or less standard agarose gel of less than 2% (g/l) agarose. The higher concentration agarose gels are, however, difficult to prepare and have not, as yet, been adopted commercially.

A high-resolution system that makes use of a prebuffered 1% (g/l) agarose gel precast into a flexible plastic support has been commercially available since 1975, and was originally marketed by Worthington Diagnostics of Freehold, New Jersey under the trademark Panagel ®. The main component of the unit is a "solid state" cooling block which absorbs the excessive heat generated by the applied potential of 200 V and avoids damage to the medium or the specimen. The Panagel ® system employs an agarose gel made up in a 1.52% barbital buffer. The same, i.e., 1.52% barbital, buffer is used as the running buffer. The Panagel ® HRE system improves resolution by employing a relatively long gel of six inches in length.

Other commercial HRE systems have also recently become available. Among these is a system marketed by Corning Medical, Palo Alto, California, which utilizes an agarose gel made up of 1% (g/l) agarose and 5% (g/l) sucrose in 0.075M barbital buffer, p.H. 8.6. The Corning running buffer contains 16.3 g of a mixture of tricine (N-tris (hydroxymethyl) methyl glycine), sodium MOPSO (3-(N-morpholino)-2-hydroxypropane sulfonic acid) and calcium lactate reconstituted to 0.075M, pH 7.3, in 1 liter of distilled or deionized water.

Barbital buffer, at pH 8.6, is accepted as the standard buffer for routine serum protein electrophoresis. Barbital, also known as veronal, is the buffer employed as the running buffer in the commercially available HRE kit marketed by Helena Laboratories, Beaumont, Texas, under the trademark TITAN ™, as well as in the prior art HRE methods previously mentioned with the exception of the HRE kit available from Corning Medical. Its superiority to; e.g., tris-glycine and borate buffers has been suggested in the orginal HRE work.

Recently hippuric acid and/or its sodium salt has been suggested generally as a substitute for barbital in buffer solutions intended for use in electrophoretic procedures. The search for a substitute for barbital stems from the fact that barbital, being a barbiturate is a "controlled substance" under the drug control laws and regulations of the United States, and under similar laws and regulations of the countries. U.S. Pat. No. 4,292,154 discloses and claims the use of hippurate, and other related compounds, as a substitute for barbital in the running buffer used in electrophoretic methods. It is not suggested that hippurate buffer is superior to barbital buffer, nor is the hippurate acid buffer suggested for use in HRE procedures other than as a substitute for the standard barbital buffer generally used in the electrophoretic separation of proteins.

SUMMARY OF THE INVENTION

The present invention provides a novel agarose gel for use in an HRE procedure. The novelty of the gel lies in the use of either sodium hippurate or glycine or combinations thereof in further combination with sodium barbital, the Tris (2-amino-2-hydroxymethyl-1,3-propanediol) in the gel buffer used to make up the agarose gel. Aspartic acid, potassium chloride, sodium azide, and ethylene glycol may also be added to the buffer which is made up in deionized or distilled water. The novel HRE gel of the present invention provides improved separation and resolution of the protein fractions of a serum sample. The improved resolution persists where a standard barbital buffer is used as the running buffer or where the gel buffer is also used as the running buffer.

DETAILED DESCRIPTION OF THE INVENTION

Figure 1:
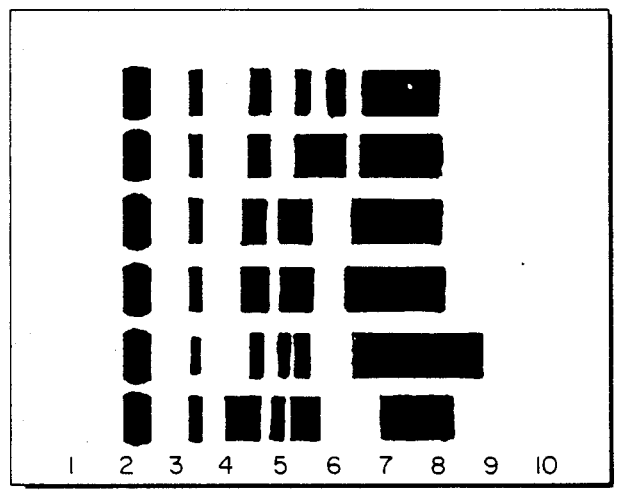

The addition of either hippuric acid (benzoylglycine), usually in the form of its sodium salt, or glycine, or combinations thereof to an agarose gel buffer has surprisingly been found to greatly improve the clarity and resolution obtained pursuant to an HRE procedure. The prior art, see, for example, Johannson, B. G., Agarose Gel Electrophoresis, *Scand. J. Clin. Lab. Invest.*, 29, (Suppl. 124), 7–19 (1972), suggests that such glycine-based buffers would result in inferior, or at best comparable, resolution to the standard barbital buffer, yet the opposite result has been achieved. The improved resolution is observed both where the gel buffer is also used as the running buffer and where the standard sodium barbital buffer is used as the running buffer. This is particularly advantageous, because the same barbital buffer can, with minor concentration and/or ionic strength adjustments, be used to run several different types of electrophoretic procedures, including HRE. Moreover, this improved separation is observed on a relatively short gel of only four inches in length.

The hippurate, glycine, or mixture of hippurate and glycine is ordinarily present in the gel buffer at approximately the same concentration as the barbital and Tris; i.e., the concentration of each such component is within a range varying by no more than 0.5% of the total concentration. Preferably, the hippurate or glycine is added to the buffer in concentrations on the order of from about 0.3% to about 2.0% (g/l) in combination with a like amount of Tris and approximately 0.3 to 1.2% (g/l) sodium barbital. It should be noted, however, that extra cooling may be required at the upper end of this range. This buffering system improves the sharpness of the bands obtained pursuant to electrophoretic separation of serum proteins on the agarose gel under typical HRE conditions.

The gel buffer may also contain an acid, such as aspartic acid or barbituric acid, to adjust pH and further improve separation, and a salt, such as potassium chloride or sodium chloride, to increase conductivity. The choice and relative concentrations of the acid and salt may easily be adjusted by those skilled in the art to obtain optimal results. Preferably the acid will be present in a concentration comparable to that of the hippurate or glycine and tris, i.e., preferably on the order of about 0.3% to about 2.0% (g/l). The salt is ordinarily present at a concentration of about 0.01% to about 0.10% (g/l).

The gel buffer may further comprise an effective amount of a preservative, such as sodium azide, although other preservatives, such as thimerosol, may be used. Again, the determination of the effective amount of the preservative is within the purview of one of ordinary skill in the art. Commonly, the preservative is added at a concentration of about 0.05% to about 0.15% (g/l).

A humectant may also be optionally added to the gel buffer. Ethylene glycol and sucrose are common humectants which prevent the gel from drying out over time. In addition, these substances increase viscosity and reduce diffusion of the protein bands. Ethylene glycol is usually included in agarose gels in concentrations of approximately 2% to about 15% (v/v) while sucrose concentrations are on the order of about 2% to about 10% (g/l).

As with all HRE gel buffers, calcium ions should be included to improve separation in the $\beta$—globulin region. Preferably, these calcium ions are added in the form of calcium lactate, although other sources of calcium ions, such as calcium acetate, may be used. Where calcium lactate is employed as the calcium ion source, the calcium lactate is preferably included in a concentration from about 0.05% to about 0.3% (g/l).

The gel is prepared in much the same manner as any standard agarose gel. The gel buffer is equally effective with standard agarose gels; i.e., less than 2% (g/l) agarose, as with high concentration agarose gels. Where standard low concentration agarose gels are prepared in accordance with the present invention, about 1% (g/l) agarose is dissolved in the gel buffer and heated to approximately 95° C., with stirring, then cooled to about 55° C. and preferably cast on either glass plates or plastic sheets. Alternatively, the agarose may first be added to deionized or distilled water and dissolved prior to the buffer ingredients being added. The buffer ingredients may be added either before or after heating. If added after heating, there is less chance of damaging the buffer ingredients, as by, e.g., hydrolysis. High concentration agarose gels are generally prepared as taught in the prior art with the gel buffer of the present invention being substituted for the buffer or deionized water used in the prior art.

The following examples are for illustrative purposes only and demonstrate the improved resolution obtained pursuant to the use of the gel buffer of the present invention.

EXAMPLE 1

Electrophoretic Separation Using Hippurate Gel Buffer

Agarose was added to deionized water at a concentration of 1% (g/l) and heated to about 95° C. to effect dissolution. After cooling to about 55° C., the following gel buffer ingredients wree added to the solution:
0.15% (g/l) Calcium lactate
0.6% (g/l) Sodium hippurate
0.62% (g/l) Sodium barbital
0.6% (g/l) Aspartic acid
0.7% (g/l) Tris
0.05% (g/l) Potassium chloride
0.1% (g/l) Sodium azide
10% (v/v) Ethylene glycol The resulting solution was then cast on 3×4 inch plastic sheets. The cast gel had a pH of approximately 8.1 or slightly higher. Six specimen samples were applied across the 3-inch direction of the gel using standard template application procedures. The gel was then placed, agarose side up, in a water-cooled support and the entire assembly inverted into a buffer containing electrode unit such that the ends of the gel were immersed in a standard barbital running buffer at about 0.15 $\mu$ionic strength. An electric potential of 200 V was applied across the 4-inch direction of the gel, and electrophoretic separation allowed to continue for about 45 minutes. The current was then stopped, the gel removed, and a standard fixative applied to the gel for approximately 10 minutes. The gel was then allowed to dry for approximately 20 minutes, followed by staining with a standard protein stain for a period of about three minutes. The gel was then destained with 5-10% acetic acid for approximately five minutes, dried, usually also for a period of about five minutes, and read. The interpretation may be visual or by automated methods such as densitometry. The results are displayed in FIG. 1.

EXAMPLE 2

Electrophoretic Separation Using Glycine Gel Buffer

Figure 2:
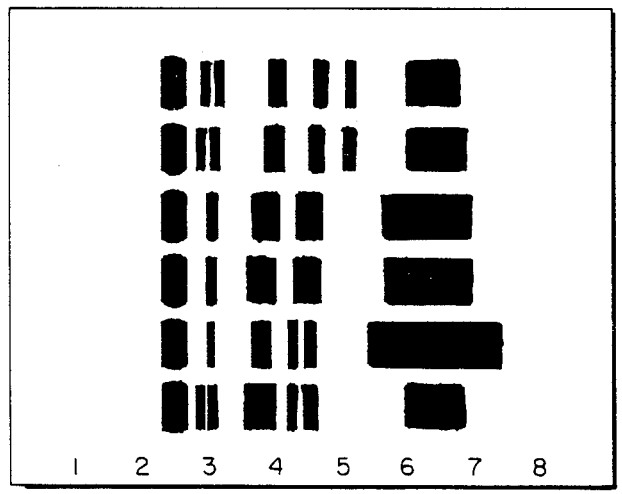

The same procedure was followed as set forth in Example 1 with the exception that the following gel buffer formulation was used:
0.15% (g/l) Calcium lactate
1.0% (g/l) Glycine
0.62% (g/l) Sodium barbital
0.6 (g/l) Aspartic acid
0.7% (g/l) Tris
0.05% (g/l) Potassium chloride
0.1% (g/l) Sodium azide
10% (v/v) Ethylene glycol
90% (v/v) Deionized water The results of this electrophoretic separation are shown in FIG. 2.

EXAMPLE 3

Electrophoretic Separation Using Hippurate/Glycine Gel Buffer

Figure 3:
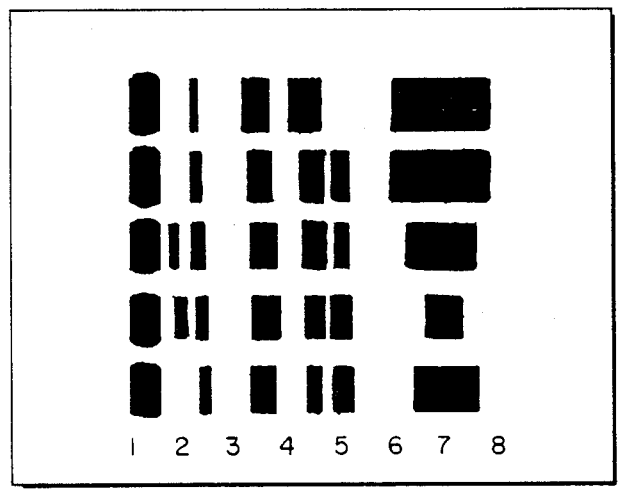

The same procedure was followed as set forth in Example 1 with the exception that the following gel buffer formulation was used:
0.15% (g/l) Calcium lactate
0.1% (g/l) Sodium hippurate
0.5% (g/l) Glycine
0.62% (g/l) Sodium barbital
0.6% (g/l) Aspartic acid
0.7% (g/l) Tris
0.5% (g/l) Potassium chloride
0.1% (g/l) Sodium azide
10% (g/l) Ethylene glycol
90% (v/v) Deionized water The results of this electrophoretic separation are shown in FIG. 3.

Other gel buffer formulations will be apparent to those skilled in the art. As this invention may be embodied in several different gel buffer formulations and agarose gels, without departing from the essential spirit of the invention, the invention is intended to be defined by the appended claims as opposed to the foregoing description

What is claimed is:

1. A buffer for an electrophoretic gel comprising barbital, 2-amino-2-hydroxymethyl-1,3-propane diol, a salt, and a resolution enhancer selected from the group consisting of hippurate, glycine and mixtures thereof.

2. The buffer of claim 1 wherein the barbital, the 2-amino-2-hydroxymethyl-1,3-propane diol and the resolution enhancer are present at approximately the same concentration.

3. The buffer of claim 39 wherein the barbital is present at a concentration of from about 0.3% to about 1.2% (g/l) and the 2-amino-2-hydroxymethyl-1,3-propane diol and resolution enhancer are each present at a concentration of from about 0.3% to about 2.0% (g/l).

4. The buffer of claim 1 wherein the salt is an alkali metal salt.

5. The buffer of claim 1 further comprising an acid.

6. The buffer of claim 5 wherein the acid is selected from the group consisting of aspartic acid and barbituric acid.

7. The buffer of claim 5 wherein the acid is aspartic acid.

8. The buffer of claim 1 wherein the alkali metal is potassium.

9. The buffer of claim 1 further comprising a source of calcium ions.

10. The buffer of claim 9 wherein the source of calcium ions is selected from the group consisting of calcium lactate and calcium acetate.

11. The buffer of claim 9 further comprising an acid.

12. An electrophoretic gel comprising agarose, water, barbital, 2-amino-2-hydroxymethyl-1,3-propane diol, a salt, and a resolution enhancer selected from the group consisting of hippurate, glycine and mixtures thereof.

13. The electrophoretic gel of claim 12 wherein the barbital, the 2-amino-2-hydroxymethyl-1,3-propane diol and the resolution enhancer are present at approximately the same concentration.

14. The electrophoretic gel of claim 12 wherein the barbital is present at a concentration of from about 0.3% to about 1.2% (g/l) and the 2-amino-2-hydroxymethyl-1,3-propane diol and resolution enhancer are each present at a concentration of from about 0.3% to about 2.0% (g/l).

15. The electrophoretic gel of claim 12 wherein the salt is an alkali metal salt.

16. The electrophoretic gel of claim 15 wherein the alkali metal is potassium.

17. The electrophoretic gel of claim 12 further comprising an acid.

18. The electrophoretic gel of claim 17 wherein the acid is selected from the group consisting of aspartic acid and barbituric acid.

19. The electrophoretic gel of claim 17 wherein the acid is aspartic acid.

20. The electrophoretic gel of claim 12 further comprising a source of calcium ions.

21. The electrophoretic gel of claim 20 wherein the source of calcium ions is selected from the group consisting of calcium lactate and calcium acetate.

22. The electrophoretic gel of claim 20 further comprising an acid.

* * * * *

UNITED STATES PATENT AND TRADEMARK OFFICE
CERTIFICATE OF CORRECTION

PATENT NO. : 4,857,163
DATED : August 15, 1989
INVENTOR(S) : Gurske, et al.

It is certified that error appears in the above-identified patent and that said Letters Patent is hereby corrected as shown below:

Col. 2, line 58 reads "...between the $\theta$- and $\gamma$- globulin." should read "...between the $\beta$- and $\gamma$- globulin.--

Signed and Sealed this

Nineteenth Day of April, 1994

Attest:

BRUCE LEHMAN

Attesting Officer     Commissioner of Patents and Trademarks